US012805876B2

(12) United States Patent
Schembre et al.

(10) Patent No.: US 12,805,876 B2
(45) Date of Patent: Nov. 24, 2026

(54) ENDOSCOPIC CLOSURE DEVICE

(71) Applicants: Drew Schembre, Orinda, CA (US); Benjamin Merrifield, Olympia, WA (US)

(72) Inventors: Drew Schembre, Orinda, CA (US); Benjamin Merrifield, Olympia, WA (US)

( * ) Notice: Subject to any disclaimer, the term of this patent is extended or adjusted under 35 U.S.C. 154(b) by 408 days.

(21) Appl. No.: 17/929,912

(22) Filed: Sep. 6, 2022

(65) Prior Publication Data

US 2023/0073110 A1 Mar. 9, 2023

Related U.S. Application Data

(60) Provisional application No. 63/241,052, filed on Sep. 6, 2021.

(51) Int. Cl.

| | |
|---|---|
| ***A61B 17/122*** | (2006.01) |
| ***A61B 17/00*** | (2006.01) |
| ***A61B 17/128*** | (2006.01) |

(52) U.S. Cl.

CPC ........ *A61B 17/122* (2013.01); *A61B 17/1285* (2013.01); *A61B 2017/0042* (2013.01); *A61B 2017/00818* (2013.01)

(58) Field of Classification Search

CPC ... A61B 17/0487; A61B 17/08; A61B 17/083; A61B 17/10; A61B 17/122; A61B 17/128; A61B 17/1285; A61B 2017/00269; A61B 2017/00641; A61B 2017/12004; A61F 5/0086; A61F 6/202–206

See application file for complete search history.

(56) References Cited

U.S. PATENT DOCUMENTS 3,746,002 A * 7/1973 Haller .................. A61B 17/282 24/518
5,366,459 A * 11/1994 Yoon .................. A61B 17/0057 606/151
5,776,147 A * 7/1998 Dolendo ............ A61B 17/1285 606/151
2006/0155310 A1* 7/2006 Binmoeller ........ A61B 17/1285 606/151
2018/0092703 A1* 4/2018 Rodriguez-Navarro ..................... A61B 90/361
2020/0093496 A1 3/2020 Ryan et al.
2021/0236127 A1* 8/2021 Yamamoto ........... A61B 17/083
2021/0330327 A1 10/2021 Saenz Villalobos et al.

* cited by examiner

*Primary Examiner* — Elizabeth Houston
*Assistant Examiner* — Lindsey Bachman

(57) ABSTRACT

A closure device with a fixed upper jaw and a pivoting lower jaw, and a hook like tooth extending from the upper jaw such that the upper jaw may be used to engage distal mucosa tissue and pull the tissue over a mucosal defect while engaging proximal tissue with the lower jaw. This configuration allowing the closure of mucosal defects that are wider than the jaw span of the closure device.

5 Claims, 7 Drawing Sheets

ENDOSCOPIC CLOSURE DEVICE

PRIORITY INFORMATION

This application claims priority to U.S. Provisional Application No. 63/241,052, filed Sep. 6, 2021.

BACKGROUND OF THE INVENTION

When lesions are removed from within the lumen of the gastrointestinal (GI) tract, resulting defects carry risk of perforation and bleeding as well as delayed wound healing. Numerous studies recommend defect closure, when possible, as a safer option than allowing the defect to scar over, known as healing by second intention. The characteristics and location of the mucosal tissue in the GI tract make closure difficult, especially when performed endoscopically instead of surgically. Endoscopic suturing tools exist but are bulky, difficult or impossible to use in many locations and expensive. Endoscopic clips, which were designed to control bleeding in the GI tract by pinching mucosa and vessels together, and have been used with varying success to close mucosal defects.

These risks are addressed by using endoscopic clips, which reduce the risk of delayed bleeding as the tissue being closed is not punctured. Currently available endoscopic clips are designed primarily to treat bleeding by pinching off vessels that are exhibiting spurting or oozing at the treatment site.

For example, U.S. Pat. No. 8,444,660B2 to Adams et al., entitled Device and Method for Through the Scope Endoscopic Hemostatic Clipping, describes a two arm, all-in-one hemostasis clip that incorporates a clip, actuator handle and shaft. The clip can open and close before deploying. The handle and shaft are disposed after the clip is deployed. This clip was designed to pinch blood vessels to stop bleeding and was not designed to close mucosal defects.

U.S. Pat. Pub. 20150190136A1 to Cohen et al., entitled Multifunctional Core for Two-Piece Hemostasis Clip, describes a two piece hemostasis clip with opening and closing capability and a mechanism that locks the clip and separates the clip from the handle and shaft. One disadvantage of this clip is that the clip must close on the tissue in order to manipulate the tissue. Thus, if the defect to be closed is wider than the mouth of the clip, another device is needed to partially close the defect before the clip may be deployed.

U.S. Pat. No. 8,764,774B2 to Sigmon, entitled Clip System Having Tether Segments for Closure, describes a clip designed for closing tissue defects but relies on two arms moving together such that it would likely release tissue if traction were applied and the clip opened.

U.S. Pat. No. 10,010,336B2 describes versions of an asymmetric and symmetric two jaw clip that has been strengthened to hold tissue more tightly however it suffers the same limitations as other clips in that it cannot hold tissue and pull it without releasing it when opened.

It is estimated that over half of all clips used in the United States are used for the aforementioned type of defect closure. When using currently available clips to close larger defects, especially defects that are wider than the open jaw span of the clip, several clips must be used beginning at an edge of the defect and "zippering" the defect closed by placing successive clips along the length of the defect. As a result, large defects, such as those over 15 mm, may require several clips to close. Many large defects will not close with even several clips. Larger defects and those surrounded by stiff tissue or thickened mucosa are often left to scar in by second intention.

OBJECTS AND SUMMARY OF THE INVENTION

The present invention is directed to providing a defect closure clip (endoscopic clip) that enables the endocscopist to reliably capture a distal side of a mucosal defect and pull it toward the endoscope and the proximal side of the defect. The defect closure clip allows the endoscopist to retain the tissue captured from the distal aspect of the defect in proximity to the proximal side of the defect, even under tension, as the jaw of the clip is opened.

The defect closure clip of the present invention differs from the endoscopic clips mentioned above in that only one arm moves, the jaws are different sizes and the tooth configuration is designed to grasp and hold tissue and pull it into position before the clip is fully deployed. The arm configurations allow the clip to retain tissue under traction even as the clip is opened. The defect closure clip further enables tissue capture of the proximal aspect of the defect, even as it retains hold of the distal edge, in order to compress and lock the two edges of the defect together.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1A:
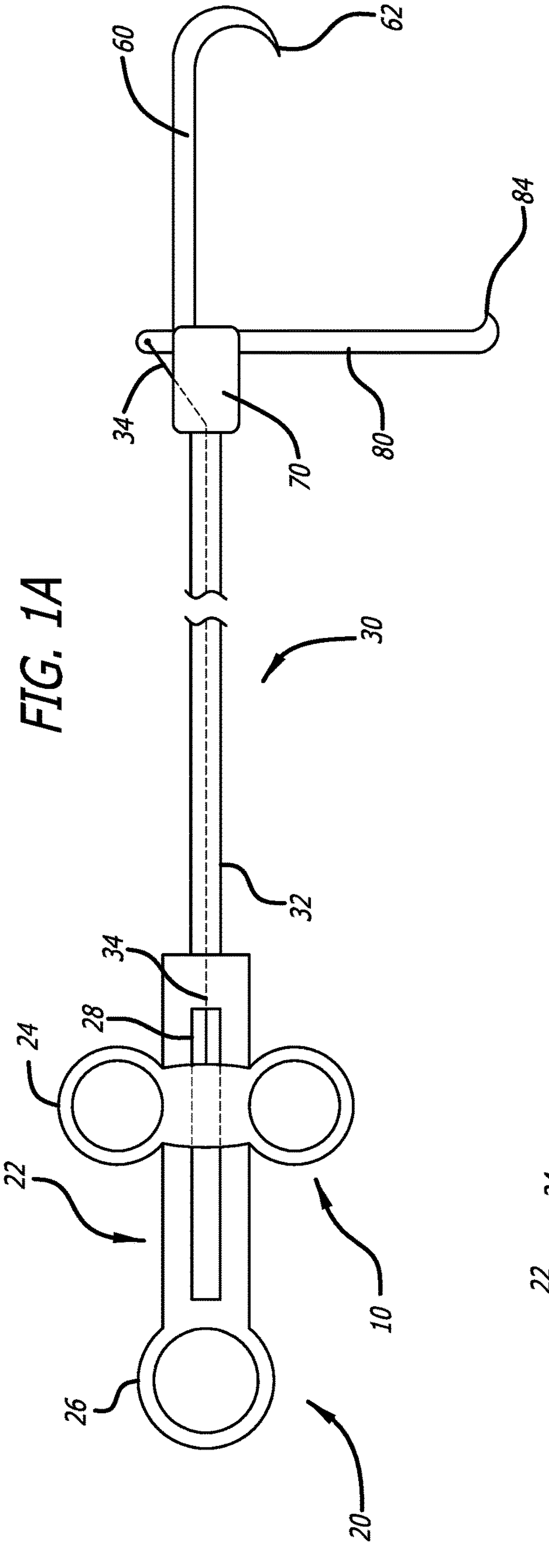
FIG. 1A is an elevation of an embodiment of the invention in an open configuration.

Specific embodiments of the invention will now be described with reference to the accompanying drawings.

This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 1B:
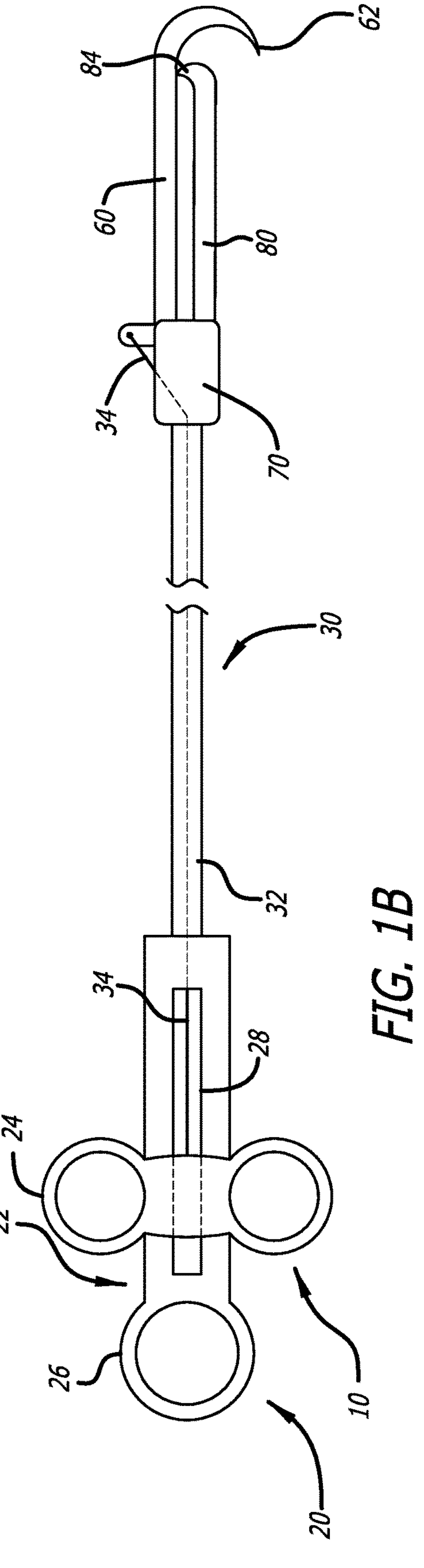
FIG. 1B is an elevation of the embodiment of FIG. 1B in a closed configuration.

As shown in FIGS. 1A and 1B, the endoscopic clip device 10 of the invention generally includes a proximal end 20 having a handle 22 and a distal end 40 that includes a detachable endoscopic clip, also referred to herein as a closure assembly 42. The proximal end 20 and the distal end 40 are joined by an insertion tube 30. The handle 22 includes a finger grip 24 and a thumb grip 26. The handle 22 and the insertion tube 30 comprise a delivery device for the closure assembly 42.

The finger grip 24 is forward (distal) of the thumb grip 26 and slides within a slot 28 in the handle relative to the thumb grip 26. The slot 28 provides access to an inner control wire 34 that is attached to the closure assembly 42 to facilitate opening and closing the closure assembly 42. Alternatively, the finger grip 24 may be connected to an outer sleeve 32 of the insertion tube 30, while the thumb grip 26 may be connected to the inner control wire 34, depending on the configuration of the closure assembly. Preferably, the configuration results in a closing action that results from the thumb grip 26 and the finger grip 24 being squeezed together as shown in FIGS. 1A and 1B. This configuration is more ergonomic and provides greater clip squeezing force.

The closure assembly 42 generally includes an upper jaw 60 and a lower jaw 80. The upper jaw 60 and the lower jaw 80 are hingedly connected by a hinge 70. In at least one embodiment, the upper jaw 60 is connected to the outer sleeve 32 such that the upper jaw 60 does not pivot relative to the insertion tube 30. In these embodiments, the upper jaw 60 may extend axially from the distal end of the insertion tube 30 or may be connected at a fixed, small angle relative to the insertion tube 30. The angle should be small (less than about 5 degree) to prevent interference or tissue trauma during insertion of the device.

The lower jaw 80 is pivotally connected to the hinge 70 and connected to the control wire 34 point on the lower jaw 80 offset distally from the hinge. In this embodiment, the thumb grip 26 and finger grips 24 would be spread apart in order to open the jaws and squeezed together in order to close the jaws of the closure assembly. In at least one embodiment, the lower jaw 80 has a range of motion that extends from closed to an angle approximately 90 degrees from the upper jaw 60.

Figure 2:
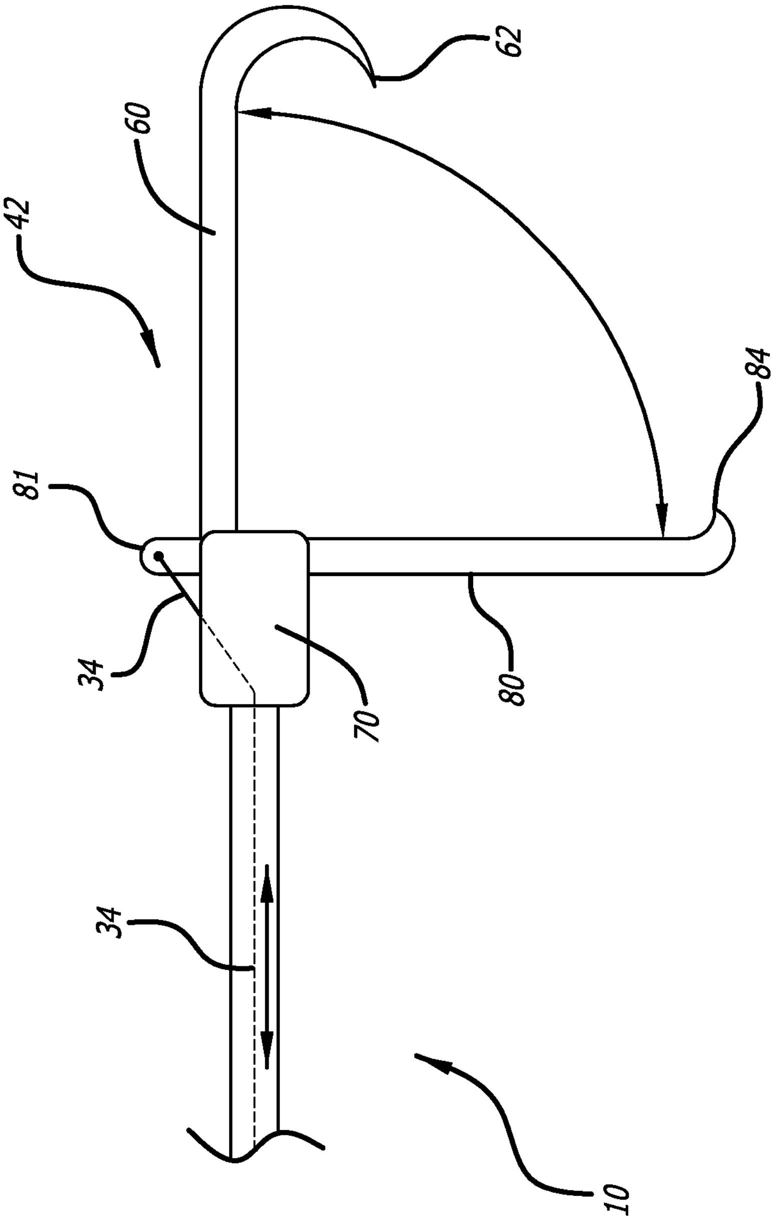
FIG. 2 is an elevation of a distal end of an embodiment of the invention in an open configuration.

FIG. 2 shows a close-up of the closure assembly 42. In the embodiment of FIG. 2, a distal end of the control wire 34 is connected to a proximal and lateral extension 81 of the lower jaw 80, while a proximal end of the control wire 34 is attached to the finger grip 24 such that depressing the thumb grip 26 (see handle shown in FIGS. 1A and 1B), shortens a distance between the thumb grip 26 and the finger grip 24, thereby pulling the control wire proximally through the outer sleeve and closing the closure assembly 42. Conversely, if a user increases the distance between the thumb grip 26 and the finger grip 24 by spreading the thumb and fingers, the control wire gets pushed distally through the outer sleeve 32, opening the jaws of the closure assembly 42.

The upper jaw 60, as stated above, extends axially from the outer sleeve 32 and may be fixed relative to the orientation of the outer sleeve 32. The upper jaw 60 further includes a distal hook-like tooth 62 that is usable to grab and manipulate tissue. The distal tooth 62 is sharp enough to easily penetrate tissue, and is angled proximally such that it may pull tissue from a distal side of a defect proximally, without significant gripping assistance from the lower jaw 80.

In at least one embodiment, the lower jaw 80 also includes a tooth 84 that can be used to grab tissue from a proximal side of the defect while the upper jaw 60 is grabbing tissue from the distal side of the defect. The lower tooth 84 may extend perpendicularly, or at a slight distal angle from perpendicular, from the lower jaw 80. The defect is closed when the closure assembly is closed. This feature allows the device to grab tissue on both sides of a defect too large to be closed by conventional clips.

Figure 3A:
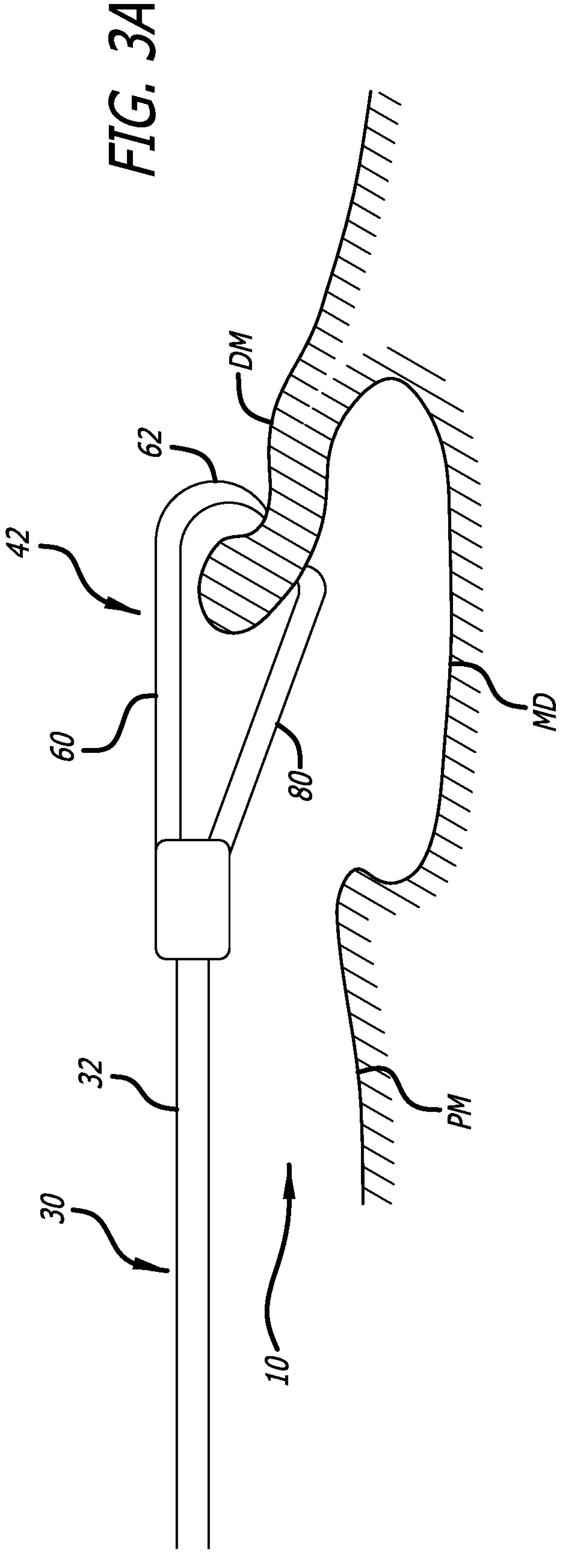
FIG. 3A is a depiction of an embodiment of a closure device grabbing tissue.
Figure 3B:
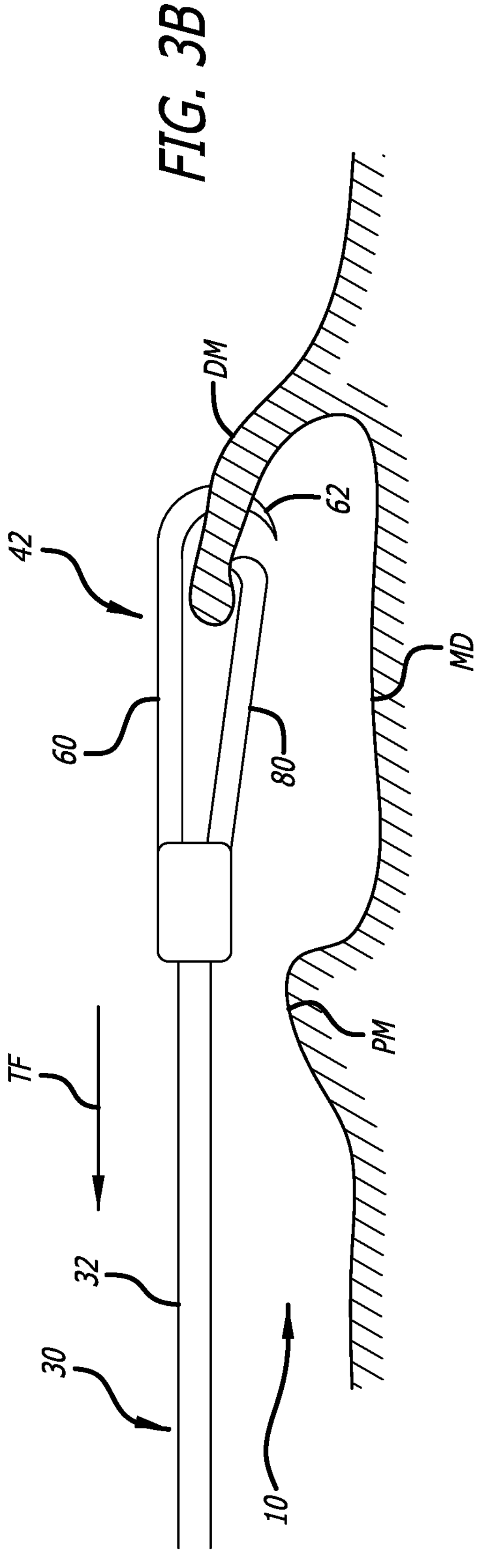
FIG. 3B is a depiction of the embodiment of FIG. 3A pulling the grabbed tissue.

FIGS. 3A and 3B depict one embodiment of the closure assembly 42 manipulating tissue using the tooth 62 of the upper jaw 60. In FIG. 3A, the device 10 has been advanced until the distal end 40 extends past a mucosal defect MD. The closure assembly has been opened enough to grasp the distal mucosa DM. The lower jaw 80, in this embodiment, presses on a bottom side of the distal mucosa DM in order to initiate engagement between the distal mucosa DM and the tooth 62 of the upper jaw 60.

In FIG. 3B, the device 10 is retracted in the proximal direction, placing a traction force on the DM depicted by the arrow TF. The tooth 62 is curved proximally to form a hook. In addition to the tissue anchoring initiated by closing the jaw on the distal edge of the tissue, the hook-shape drives the tooth 62 into the tissue when the device 10 is pulled proximally, in the direction of the arrow in FIG. 3B. Once the tooth 62 has fully engaged the DM tissue, as shown in FIG. 3B, the lower jaw 80 does not need to contact the DM as long as a proximal traction force is being applied. This allows the lower jaw 80 to be used to engage the proximal mucosa PM.

Figure 4A:
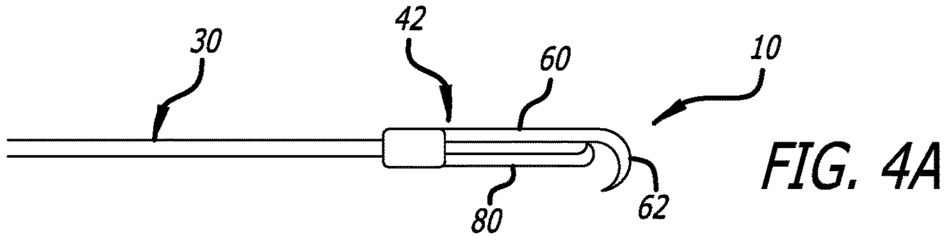
FIG. 4A is a depiction of a first step of an embodiment of a method of the invention.
Figure 4B:
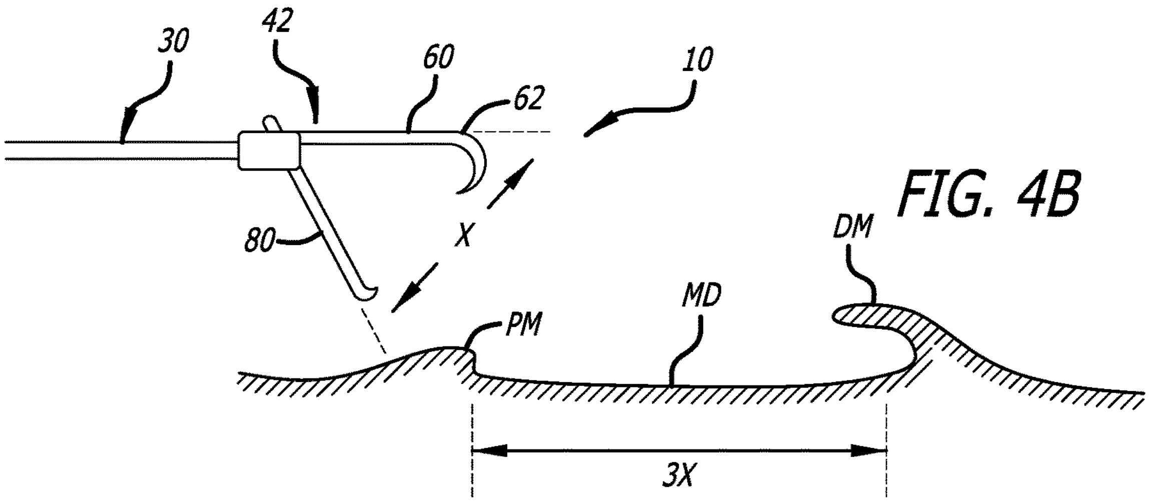
FIG. 4B is a depiction of a second step of a method of the invention.

An example of a method of using the device is shown in FIGS. 4A-G. As shown in FIG. 4B, the width of the mucosal defect MD is significantly greater (in this case three times greater) than the span X of the device 10. In FIG. 4A, the device 10 is shown in a closed configuration for purposes of navigating to the MD. The curved tooth 62 creates a curved, blunt distal end in the closed configuration.

Figure 4C:
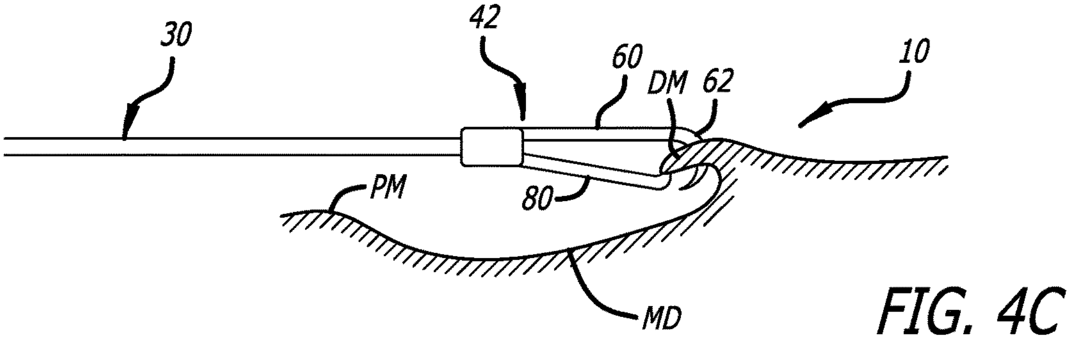
FIG. 4C is a depiction of a third step of a method of the invention.

In FIG. 4B, the user has opened the closure assembly 42, rotating the lower jaw 80 away from the upper jaw 60. In FIG. 4C, the DM is being engaged by positioning the upper tooth 62 over the DM and using the lower jaw 80 to create enough resistant force on the DM to allow the upper tooth 62 to begin penetrating the tissue of the DM.

Figure 4D:
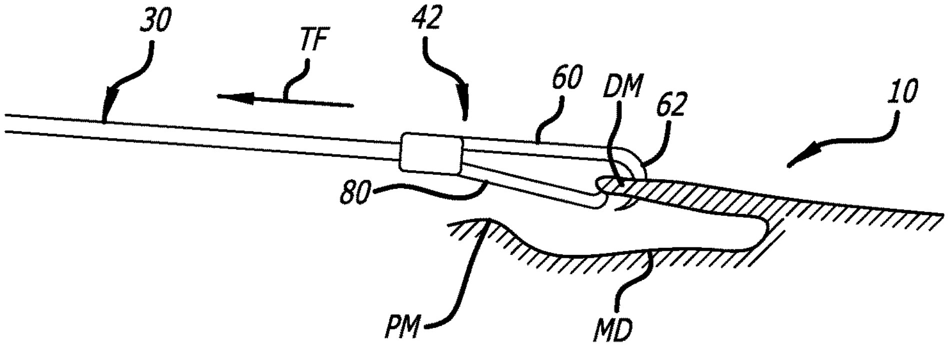
FIG. 4D is a depiction of a fourth step of a method of the invention.
Figure 4E:
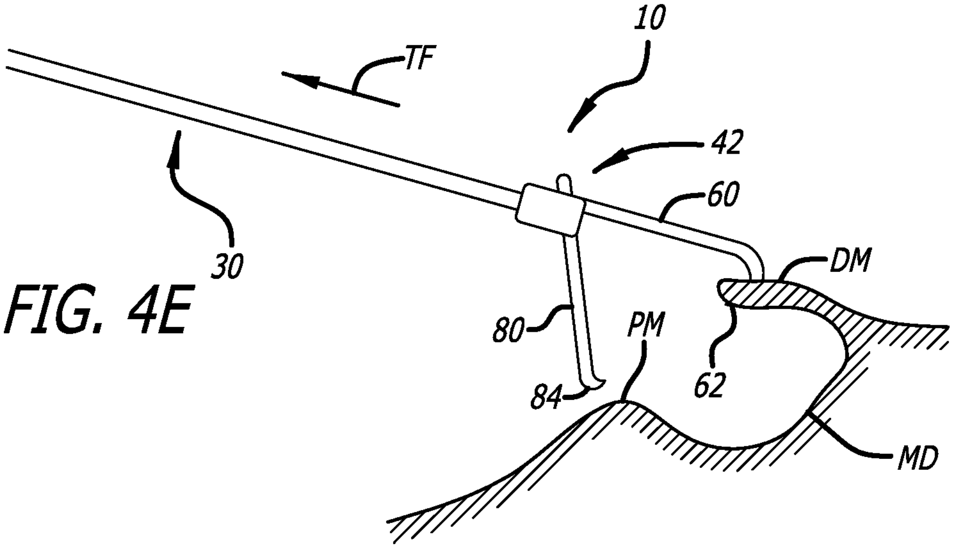
FIG. 4E is a depiction of a fifth step of a method of the invention.

In FIG. 4D, a traction force is placed on the DM in the direction of the arrow TF. The DM, as a result, is pulled over the MD toward the PM, reducing the span of the MD. As illustrated in FIG. 4E, as long as the traction force TF is maintained, the lower jaw 80 may be opened without disengaging the DM tissue due to the hook shape of the upper tooth 62.

Figure 4F:
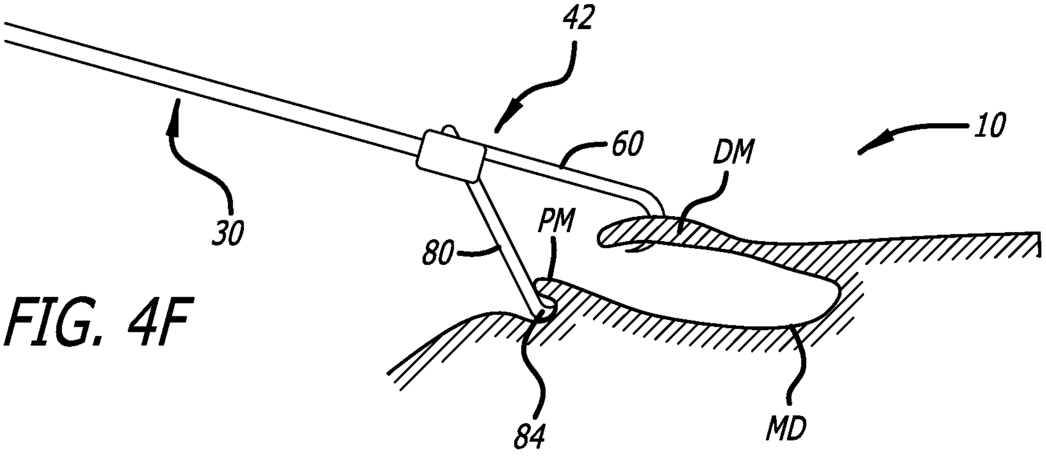
FIG. 4F is a depiction of a sixth step of a method of the invention.

In FIG. 4F, the lower tooth 84 of the lower jaw 80 has engaged tissue of the PM. The upper jaw 60 is fixed relative to, and in line with, the insertion tube 30. Thus the user can maintain traction force TF on the upper jaw 60, while freely operating the lower jaw 80. By squeezing the thumb grip 26 and the finger grip 24 together, the lower jaw 80 pivots around the hinge 70, causing the lower tooth 84 to engage the tissue of the PM as it swings toward the upper jaw 60.

Figure 4G:
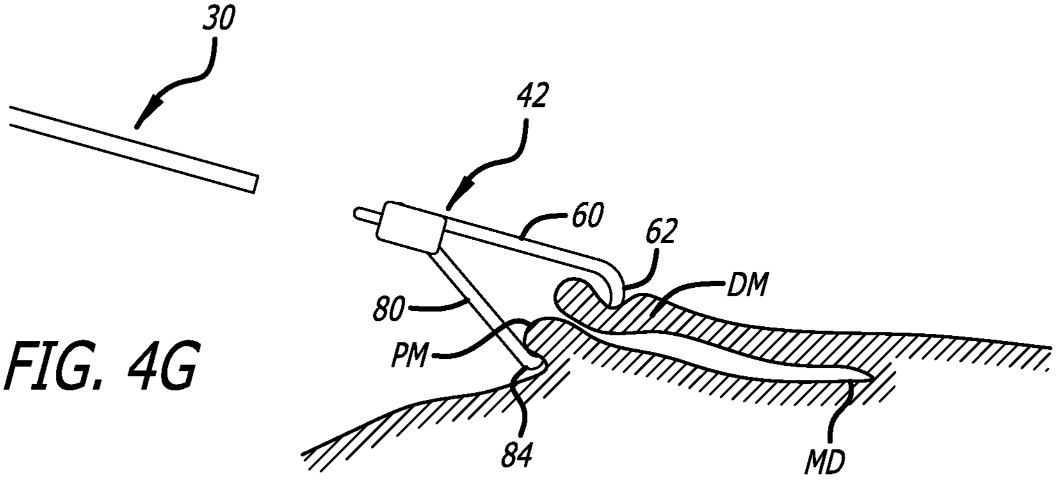
FIG. 4G is a depiction of a seventh step of a method of the invention.
Figure 5:
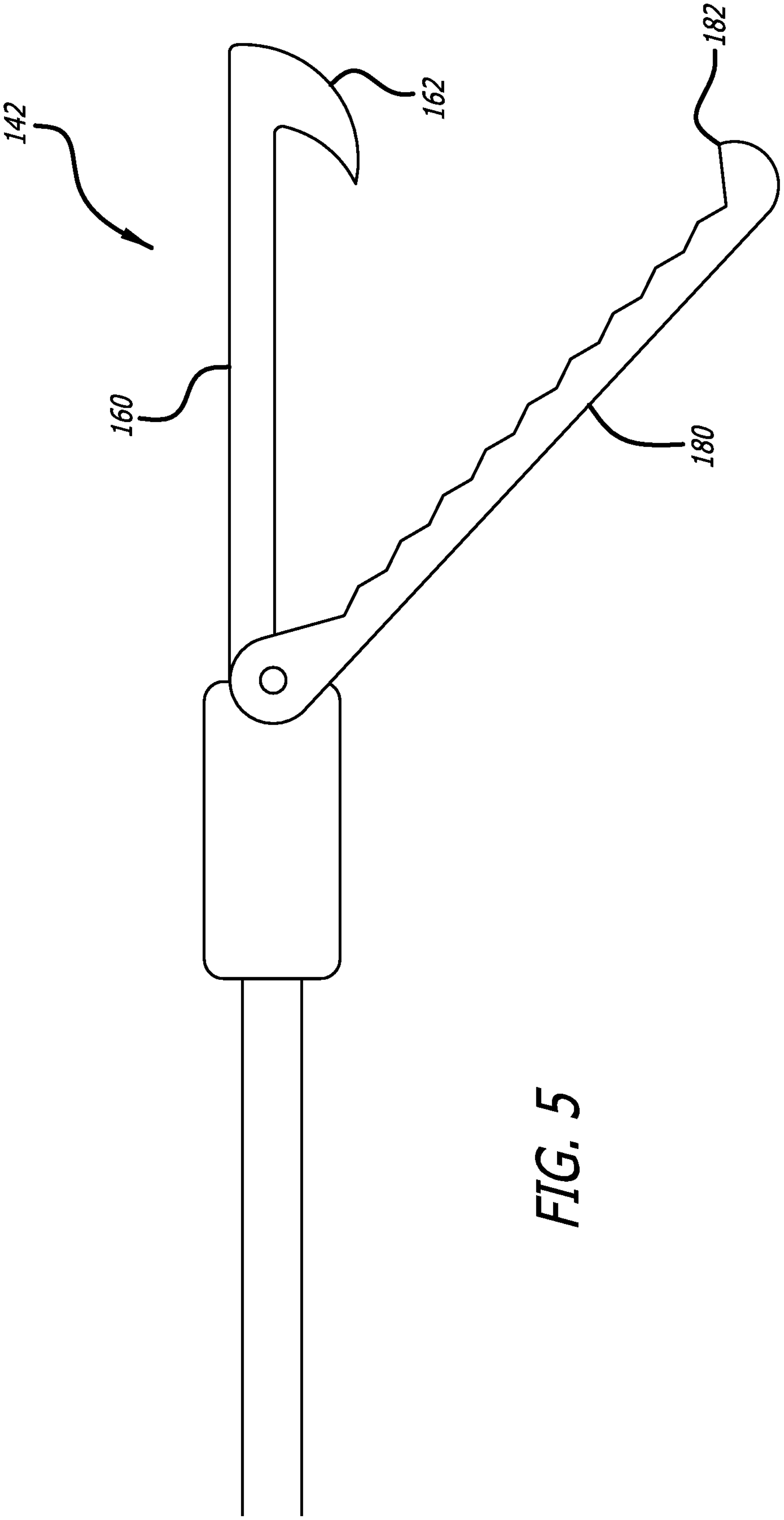
FIG. 5 is an elevation of a distal end of an embodiment of the invention in an open configuration.
Figure 6A:
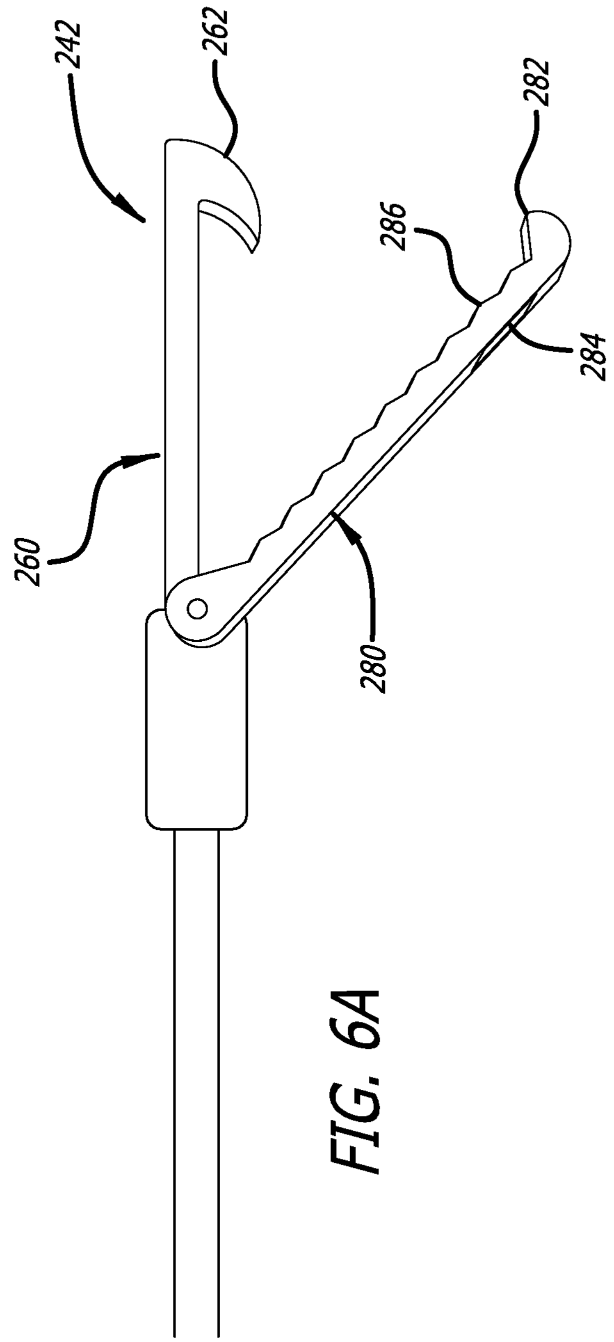
FIG. 6A is an elevation of a distal end of an embodiment of the invention in an open configuration; and, FIG. 6B is an elevation of a distal end of the embodiment of FIG. 6A in a closed configuration.
Figure 6B:
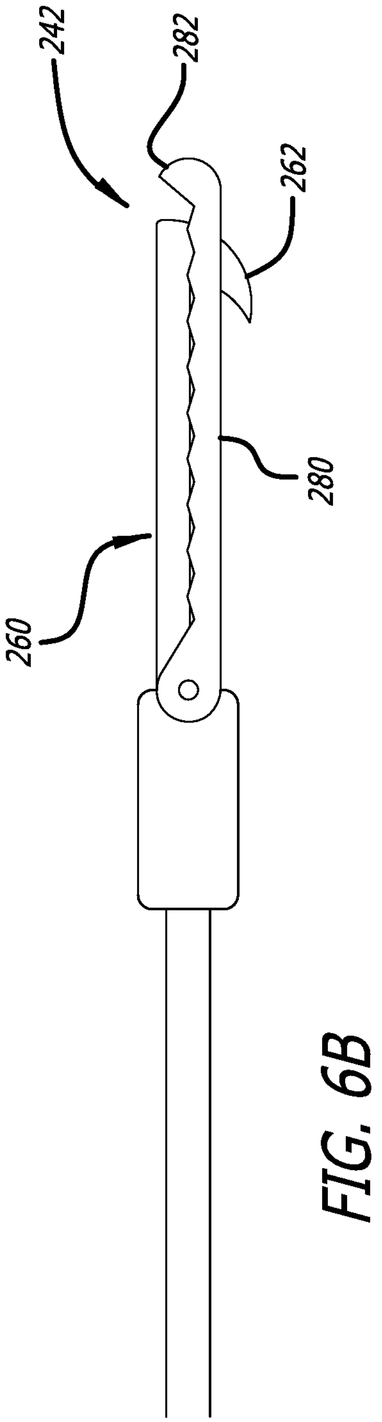

In FIG. 4G, the closure assembly 42 is closed and locked, thereby keeping the MD closed. The locking mechanism may be a metal sleeve that is pushed over the proximal ends of the upper and lower jaws, a ratcheting system, or other locking devices such as those commonly used on clips and known in the art. The pressure of the DM against the PM will cause the two tissue segments to fuse over time and the MD will be eliminated. Once the user is satisfied with the placement of the closure assembly 42, a disconnect 90 is used to separate the closure assembly 42 from the insertion tube 30 to allow the insertion tube 30 to be removed, leaving the closure assembly 42 in place. The disconnect 90 can be a threaded connection between the insertion tube and the closure assembly 42 or similar connection, as is known in the art. The control wire 34 can similarly be disconnected from the closure assembly 42 by including a breakaway point that shears off when enough squeezing force is used on the handle. If, before deployment, the clip is felt to be in an undesireable position, it can be opened and the upper tooth disengaged by reversing the actions and pushing the clip away from the distal margin, FIGS. 5, 6A and 6B show alternative embodiments of the closure assembly, specifically, the upper and lower jaws. In FIG. 5 an embodiment 142 of the closure assembly is shown in which there is a shorter upper jaw 160 and a longer lower jaw 180. Both the upper jaw 160 and the lower jaw 180 have hook-like teeth 162 and 182, respectively. A closure assembly with a longer lower jaw 180 may be better suited for mucosal defects in which the distal mucosa and/or proximal mucosa are of unmatched lengths or configurations requiring greater reach with the lower jaw.

FIGS. 6A and 6B show an embodiment 242 of a closure assembly that is similar to the embodiment 142 of FIG. 5 in that there is a lower jaw 280 that is longer than the upper jaw 260. The upper jaw 260 has an elongated tooth 262 that passes through a corresponding fenestration 284 in the lower jaw 280. Additionally, the lower jaw 280 is shown with a serrated edge 286 in addition, or instead of, a lower tooth 282.

Although the invention has been described in terms of particular embodiments and applications, one of ordinary skill in the art, in light of this teaching, can generate additional embodiments and modifications without departing from the spirit of or exceeding the scope of the claimed invention. For example, the serrated edge 286, can be incorporated into any of the embodiments shown. This is a non-limiting example of the application of a feature of one embodiment being applied to other embodiments, as one skilled in the art will understand. Accordingly, it is to be understood that the drawings and descriptions herein are proffered by way of example to facilitate comprehension of the invention and should not be construed to limit the scope thereof.

What is claimed is:

1. A device for closing a tissue defect having proximal tissue on a proximal side of the defect and distal tissue on a distal side of the defect comprising:

a handle including a thumb grip and a finger grip at a proximal end of the device;

an insertion tube;

a closure assembly at a distal end of the device detachably connected to the insertion tube and including:

an stationary jaw orientationally fixed to the insertion tube;

a moveable jaw hingedly connected to the stationary jaw with a hinge such that the moveable jaw is able to pivot in relation to the stationary jaw between an open position and a closed position, the hinge being located distal of a proximal end of the moveable jaw to form an extension between the hinge and the proximal end of the moveable jaw; and a tissue penetrating stationary tooth extending from the stationary jaw in a direction toward the moveable jaw and toward the proximal end of the moveable jaw; and a control wire extending from the handle, through the insertion tube, and connected to the extension on the moveable jaw, the extension displaced laterally from the hinge when the clip is open to provide leverage, such that said closed position is attained by squeezing the thumb grip toward the finger grip.

2. The device of claim 1 wherein the stationary jaw is longer than the moveable jaw.

3. The device of claim 1 wherein the moveable jaw is longer than the stationary jaw.

4. The device of claim 3 wherein the moveable jaw comprises a fenestration through which the stationary tooth passes when the closure assembly is in the closed position.

5. The device of claim 1 further comprising a moveable tooth extending from the moveable jaw toward the stationary jaw.

* * * * *